United States Patent [19]

Yamashita et al.

[11] 4,279,795

[45] Jul. 21, 1981

[54] HYDROPHILIC-HYDROPHOBIC GRAFT COPOLYMERS FOR SELF-REINFORCING HYDROGELS

[75] Inventors: Shuzo Yamashita; Kyoichiro Shibatani; Kiochi Takakura; Kiyokazu Imai, all of Kurashiki, Japan

[73] Assignee: Kuraray Co., Ltd., Kurashiki, Japan

[21] Appl. No.: 429,207

[22] Filed: Dec. 28, 1973

[30] Foreign Application Priority Data

Dec. 29, 1972 [JP] Japan .................................... 48-3150
Feb. 14, 1973 [JP] Japan .................................... 48-18634

[51] Int. Cl.$^3$ ............................................... C08L 51/00
[52] U.S. Cl. ............................. 260/29.6 RW; 525/311; 525/303; 525/301; 525/296; 525/292; 525/279; 424/81; 424/78; 351/160 R; 351/160 H; 260/29.6 RB; 128/68
[58] Field of Search ................. 260/885, 886, 29.6 RB, 260/29.6 RW; 525/279, 292, 296, 301, 303, 311

[56] References Cited

U.S. PATENT DOCUMENTS

| | | | |
|---|---|---|---|
| 2,808,388 | 10/1957 | Hellmann ............................. | 260/886 |
| 2,991,269 | 7/1961 | Nozaki ................................. | 260/885 |
| 3,390,206 | 6/1968 | Thompson et al. ................... | 260/881 |
| 3,450,796 | 6/1969 | Griffin ................................. | 260/885 |
| 3,514,500 | 5/1970 | Osmond et al. ...................... | 260/881 |
| 3,721,657 | 3/1973 | Seiderman .......................... | 260/885 |
| 3,745,042 | 7/1973 | Lim et al. ....................... | 117/138.8 A |
| 3,786,116 | 1/1974 | Milkovich et al. ................... | 260/886 |
| 3,841,985 | 10/1974 | O'Driscoll et al. .................. | 260/885 |
| 3,928,255 | 12/1975 | Milkovich et al. ............... | 260/2.5 R |

*Primary Examiner*—Carman J. Seccuro
*Attorney, Agent, or Firm*—Burns, Doane, Swecker & Mathis

[57] ABSTRACT

Materials for forming a hydrogel when contacted with water having improved anti-thrombogenic properties and a highly improved mechanical strength are obtained by the copolymerization of a free radical-polymerizable vinyl monomer capable of forming a hydrophilic polymer and a hydrophobic macromolecular compound having a chain-terminated polymerizable double bond and a molecular weight of 1,000 to 100,000.

13 Claims, 1 Drawing Figure

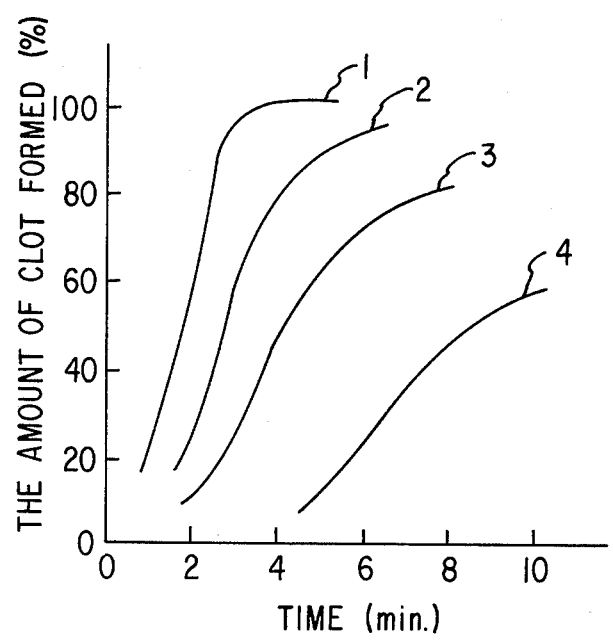

HYDROPHILIC-HYDROPHOBIC GRAFT COPOLYMERS FOR SELF-REINFORCING HYDROGELS

BACKGROUND OF THE INVENTION

1. Field of the Invention

This invention relates to a material useful as a hydrogel, i.e., a macromolecular material swollen with water. More particularly, the invention relates to a self-reinforcing hydrogel material having a high mechanical strength.

2. Description of the Prior Art

The term "hydrogel" as used herein indicates a macromolecular material having absorbed water therein, wherein at the equilibrium of swelling, the water absorption is at least 10%, preferably at least 20%, calculated according to the following equation:

$$\text{Water absorption (\%)} = \frac{\text{wet polymer weight} - \text{dry polymer weight}}{\text{dry polymer weight}} \times 100$$

It is well known to prepare insoluble hydrogels by copolymerizing hydrophilic monomers such as glycol acrylate, glycol methacrylate, methacrylamide, acrylamide and the like, with cross-linking agents which are soluble in the monomer mixture (See, e.g., U.S. Pat. Nos. 2,976,576 and 3,220,960). It is also known to prepare insoluble hydrogels by copolymerizing vinyl ester monomers with cross-linking agents which are soluble in the monomer mixture and saponifying the resultant copolymer. It is moreover known that because of their hydrophilic characteristics, such materials are very valuable as hydrogel materials. Particularly, hydrogels exhibit good compatibility with the human body without stimulating the tissue or mucosa thereof, and they have attracted attention as a medical material. For example, hydrogels have been used for manufacturing contact lenses, various prostheses, pessars, implants containing biologically active substances, coatings of artificial dentures, coatings of surgical catheters, dialysis membranes for blood and other articles which are used in contact with the tissue or mucous membranes of the human body, etc.

Moreover, hydrogels are useful in other fields and for other purposes, such as for sizing synthetic fibers, for manufacturing membranes for dialysis and ultra-filtration, for chromatographic gels, etc. However, conventional hydrogels derived from polymers such as mentioned above are generally poor in mechanical strength and this defect has been a great obstacle to actual utilization of such hydrogels in the wet state, and in addition, they generally possess insufficient anti-thrombogenic properties.

Much research has been directed toward solving these problems of hydrogels of the above type, but the results have generally been unsatisfactory. For example, it is known that the mechanical strength of such hydrogels may be improved by copolymerization with diesters, by adding inorganic fillers thereto, etc. However, hydrogels thus obtained are not satisfactory, particularly in the wet state.

SUMMARY OF THE INVENTION

It is therefore a primary object of the present invention to provide a hydrogel material which is free of the above defects.

It is another object of the invention to provide a hydrogel material having a high mechanical strength.

It is yet another object of the invention to provide a hydrogel material having a high mechanical strength while, at the same time, having good anti-thrombogenic properties.

Other objects and advantages will become apparent from the ensuing description.

It has now been found that it is possible to obtain a material useful as a hydrogel and having improved anti-thrombogenic properties and a highly improved mechanical strength, while the desirable properties of the hydrogel of the hydrophilic polymeric materials are completely retained, if branches of a hydrophobic macromolecule having a suitable chain length are appropriately introduced into the main chain of the hydrophilic polymer. Namely, according to the present invention, it has been found that the above objects can be attained by a material useful as a self-reinforcing hydrogel comprising a copolymer of (A) a free radical polymerizable monomer capable of forming a hydrophilic polymer with (B) a hydrophobic macromolecular compound having a polymerizable double bond at the end of its molecule and having a molecular weight of 1000 to 100,000. If necessary, the resulting copolymer may be saponified.

BRIEF DESCRIPTION OF THE DRAWING

The FIGURE illustrates the anti-thrombogenic properties of the copolymer (of the invention) produced in Example 2 and other materials, for comparison.

DESCRIPTION OF THE PREFERRED EMBODIMENTS

The component (A) of the copolymer of the present invention includes any and all vinyl monomers which are capable of forming a hydrophilic polymer by free radical polymerization. Since free radical polymerization per se is well known, and since hydrophilic polymers can easily be identified by their properties, those skilled in the art will realize which monomers are included in the above classification. Broadly therefore, all such vinyl monomers having these capabilities are included.

More specifically, the free radical-polymerizable vinyl monomers included in component (A) may conveniently be classified into the following three groups.

The first group includes a hydrophilic (meth)acrylic monomer represented by the general formula:

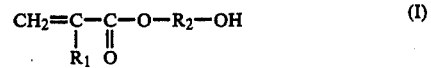

wherein $R_1$ represents a hydrogen atom or a methyl group; and R represents an alkylene group (preferably having 2 to 4 carbon atoms), or the group $-CH_2CH_2(OCH_2CH_2)_n-$ in which n is an integer of 1 to 30. Typical examples of the hydrophilic (meth)acrylic monomer represented by the general formula (I) are hydroxyethyl acrylate, hydroxyethyl methacrylate, hydroxypropyl acrylate, hydroxypropyl methacrylate, hydroxybutyl acrylate, hydroxybutyl methacrylate, polyethylene glycol monoacrylate and polyethylene glycol monomethacrylate.

The second group includes water-soluble vinyl monomers having at least one nitrogen atom. The term "water-soluble vinyl monomer having at least one nitrogen atom" as used herein indicates a vinyl monomer containing at least one nitrogen atom which is water-miscible to the extent that at least 10% by weight, preferably at least 30% by weight, based on the weight of monomer, of water is uniformly miscible with the monomer at room temperature (30° C.). As the nitrogen-containing, water-soluble vinyl monomer to be used in this invention, there may be exemplified N-mono-substituted acrylamides such as acrylamide, methacrylamide, N-methylacryl-amide, N-ethylacrylamide, N-methylolacrylamide, N-hydroxyethylacrylamide and diacetone acrylamide; N,N-di-substituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide and N,N-dihydroxyethylacrylamide; heterocyclic compounds such as N-acryloylmorpholine, N-acryloylpiperidine and N-acryloylpyrrolidone; N-vinyl heterocyclic compounds such as N-vinyl-pyrrolidone and N-vinylpiperidine; aminoethyl acrylate; aminoethyl methacrylate; N-methylaminoethyl acrylate; N-methylaminoethyl methacrylate; N,N-dimethylaminoethyl acrylate; N,N-dimethylaminoethyl methacrylate; and 2-hydroxy-3-methacryloxypropyl quaternary ammonium salts, vinylpyridine quaternary ammonium salts and dimethylaminoethyl methacrylate quaternary ammonium salts.

The third group includes vinyl esters of organic acids such as vinyl formate, vinyl acetate, vinyl monochloroacetate, vinyl trichloroacetate, vinyl propionate and vinyl butyrate. Vinyl acetate and vinyl formate are especially preferred. When such vinyl esters are polymerized and the resulting polymer is saponified, there is obtained a hydrophilic polymer.

It is not intended to limit the invention to the specific monomers given above in each group, since these are only exemplary. Rather, the intention is to include all vinyl monomers which satisfy formula (I), or which contain at least one nitrogen atom (and are water-soluble to the extent indicated) or which are vinyl esters.

In this invention, the free radical-polymerizable vinyl monomer capable of forming a hydrophilic polymer is used to form the main chain of a hydrophilic polymer hydrogel, but in order to improve certain properties (adjustment of the water absorption in the hydrogel, improvement of the handling stability of the dry gel, improvement of the transparency of the hydrogel, and improved biocompatibility and the like) of such polymers formed by homopolymerization or copolymerization of these monomers, other polymerizable hydrophilic and hydrophobic monomers may sometimes be added as modifiers in amounts not exceeding an amount equimolar to the free radical-polymerizable vinyl monomer capable of forming a hydrophilic polymer. Such "modifier monomers" include monomers which are copolymerizable with the free radical-polymerizable vinyl monomer, such as ordinary vinyl monomers, diene monomers and the like. Examples of such modifier monomers include (meth)acrylic acid, methoxyethyl (meth)acrylate, ethoxyethyl (meth)acrylate, methyl (meth)acrylate, ethyl (meth)acrylate, propyl (meth)acrylate, n-butyl (meth)acrylate, (α-methyl)styrene, (meth)acrylonitrile, vinyl esters, vinyl ethers, ethylene, propylene, butene, isoprene, butadiene and maleic anhydride. The designation "(meth)" indicates that either the acrylate or methacrylate may be used.

In this invention, a hydrophobic macromolecular compound having a chain-terminated polymerizable double bond and a molecular weight of 1,000 to 100,000 is used to introduce branches of a hydrophobic macromolecule into the main chain of the hydrophilic polymer. Thus, the above-mentioned free radical-polymerizable vinyl monomer capable of forming a hydrophilic polymer is copolymerized with the polymerizable double bond present at the chain end of said hydrophobic macromolecular compound. Typical examples of the hydrophobic macromolecular compound to be used in this invention are those which have the following general formulae;

$$R(CH_2-CH)_nCH_2-CX=CH_2 \quad (II)$$
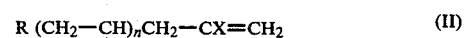

or $$R(CH_2-CH)_nCH_2-CH_2-O-\underset{\underset{O}{\|}}{C}-CX=CH_2 \quad (III)$$
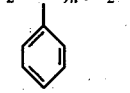
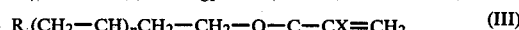

wherein R is an alkyl group of 1 to 8 carbon atoms, e.g., a butyl group, X stands for a hydrogen atom or an alkyl group of 1 to 4 carbon atoms, and n is an integer of from 10 to 1,000.

The above compounds (II) and (III) are polymeric styrene compounds having a reactive double bond at their molecular end. In addition to the above compounds, polymers of the α-methylstyrene, butadiene, isoprene, methyl methacrylate, methyl acrylate, acrylonitrile and methacrylonitrile type which have a polymerizable double bond at the molecular end may be used effectively. These hydrophobic macromolecular compounds can be prepared, for instance, by the method disclosed in published Japanese patent application Specification No. 21486/72, namely, by a method comprising reacting a terminater having a polymerizable double bond with the terminal ends of living polymers prepared by the anionic polymerization of said monomer. As the terminater, there may be exemplified vinyl haloalkyl ethers having up to 6 carbon atoms in the alkyl group, vinyl esters of haloalkanoic acids having up to 6 carbon atoms, allyl halides, acrylyl halides, methacrylylhalides, halomaleic anhydrides, halomaleic acid esters, vinyl halides and halovinyl silanes. The halogen can be any of chlorine, fluorine, bromine and iodine, but the halogen group in such terminal coupling agents is preferably a chloro group.

The above-mentioned anionic polymerization method has the advantage of easily giving the hydrophobic macromolecular compound having a narrow molecular weight distribution and desirable molecular weight.

Other typical examples of the said hydrophobic macromolecular compounds to be used in this invention are those which have the following general formulae:

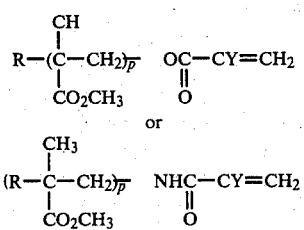
(IV)

or

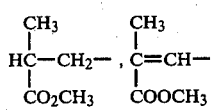
(V)

wherein R is a terminal group such as $$HC{-}CH_2{-}\underset{CO_2CH_3}{\overset{CH_3}{|}}, \quad C{=}CH{-}\underset{COOCH_3}{\overset{CH_3}{|}}$$

Y stands for a hydrogen atom or an alkyl group of 1 to 4 carbon atoms, and p is an integer of 10 to 10,000.

The above compound is polymethyl methacrylate having a reactive double bond at its molecular end. The above-mentioned macromolecular compounds IV and V may be prepared by a method comprising reacting a suitable agent having a polymerizable double bond such as (meth)acrylyl chloride with the terminal hydroxy or amino group of a hydrophobic polymer. These hydrophobic polymers having chain-terminated hydroxy or amino groups may be prepared by a free radical polymerization of the above monomer initiated by hydrogen peroxide or a redox system such as hydrogen peroxide and ferrous salts, hydrogen peroxide and ferric salts, hydroxylamine and titanous salts, or hydrazine and titanous salts in aqueous solution. According to the above-mentioned polymerization methods, it is confirmed that the obtained polymer has one hydroxy group or one amino group per molecule (Palit et al, J. Macromol. Sci., C2 225 (1968)). The hydrophobic polymer having an amino group at the molecular end may be also prepared by the polymerization of the above monomer with sodium as the initiator in liquid ammonia (Smets et al, J. Polymer Sci., 55, 767 (1961)).

The thus-obtained hydrophobic polymer having a hydroxy group or an amino group at the molecular end is then dissolved in a solvent therefor, e.g., pyridine or hexamethyl phosphoramide, and reacted with a large amount of an acid chloride having a polymerizable double bond, e.g., acrylyl chloride or methacrylyl chloride, etc., under a nitrogen atmosphere for 1 to 5 hours, preferably 2 to 3 hours, at a temperature of from 40° to 70° C., preferably from 50° to 60° C., with stirring, and there is obtained a hydrophobic macromolecular compound having a polymerizable double bond at the molecular end thereof.

The above hydrophobic polymers are only intended to be exemplary, it being the intention that all polymerizable double bond chain-terminated polymers are useful in the present invention, as long as they are hydrophobic to the extent shown below. In other words, in order for such macromolecular compounds to give a copolymer (with the hydrophilic monomer) which absorbs water and swells, thereby providing a hydrogel having an improved mechanical strength (improved as compared with the case of the hydrophilic polymer free of such branches), said macromolecular compound used to form branches should be hydrophobic and be hardly swollen with water. More specifically, when said hydrophobic macromolecular compound is soaked in water maintained at 30° C., it should exhibit an equilibrium water absorption of less than 10%.

Further, this hydrophobic macromolecular compound should have a molecular weight of from 1,000 to 100,000. If the molecular weight is lower than 1,000, the self-reinforcing property is low in the resulting hydrogel, and the reduction of the equilibrium water absorption becomes great when compared to that based on the same weight ratio of the bonded hydrophobic macromolecular compound to the hydrophilic backbone polymer. On the other hand, when the molecular weight of the hydrophobic macromolecular compound exceeds 100,000, the self-reinforcing property is lowered when compared to that based on the same weight ratio of the bonded hydrophobic macromolecular compound to the hydrophilic backbone polymer. The preferred molecular weight of the hydrophobic macromolecular compound is within a range of from 2,000 to 50,000. The molecular weight referred to herein is one determined by the vapor pressure method or the osmotic pressure method.

When the polymerizable, hydrophobic macromolecular compound is copolymerized with the free radical-polymerizable vinyl monomer capable of forming a hydrophilic polymer (and, optionally, a small amount of a modifier monomer), the mechanical strength of a hydrogel derived from the resulting copolymer is improved. The weight ratio of the hydrophobic macromolecular compound in the hydrogel-constituting polymeric material can be varied over a wide range, i.e., 5-80%, based on the weight of the copolymer, depending upon the desired properties of the resulting copolymers. The preferred ratio is 10-50% by weight. More specifically, when the content of the hydrophobic macromolecular compound in the copolymer is at least 5% by weight, the effect of its addition becomes definite (i.e., noticeable), and when the content is within the range of 10 to 30% by weight, the mechanical strength (the mechanical strength when converted to a hydrogel) is greatly improved and good compatibility with the human body can be obtained with less reduction of the water-absorbing property. At the same time, the anti-thrombogenic property thereof is greatly improved.

The copolymerization of the hydrophobic macromolecular compound having a polymerizable double bond at its molecular chain end with the free radical-polymerizable vinyl monomer capable of forming a hydrophilic polymer (and optionally a small amount of a modifier monomer) can be performed by a bulk solution, emulsion or suspension polymerization process, all of which are known per se. In each case, it is desirable that after completion of the polymerization, any remaining unreacted hydrophobic macromolecular compounds be removed. This removal may be accomplished by a solvent extraction method or the like. When the copolymerization is a bulk polymerization method and the resulting copolymer is formed in situ into a shaped article, it is especially desirable to add a cross-linking agent to the copolymerization reaction system, because the addition of the cross-linking agent improves the properties of the final hydrogel. A monomer having two or more functionalities in one molecule is used as the cross-linking agent. For instance, there may be employed N,N-methylene-bis-(meth)acrylamide, ethyleneglycol di-(meth)acrylate, diethyleneglycol di-(meth)acrylate and divinyl benzene and the like. The concentration of the cross-linking agent depends on the degree of cross-linking desired, and a preferred concentration is within a range of from 0.1 to 2% by weight, based on the weight of monomers.

The solution polymerization method is the most common polymerization method and is therefore preferred. In this case, the polymerization solvent is preferably selected from those solvents capable of dissolving any one of the free radical-polymerizable vinyl monomer (capable of forming a hydrophilic polymer), the modifier monomer (modifier), the hydrophobic macromolecular compound (having a polymerizable double bond at its molecular chain end) or the copolymer formed by the reaction thereof.

Emulsion polymerization and suspension polymerization, as well as bulk polymerization, are advantageous when the hydrophobic macromolecular compound (having a polymerizable double bond at its molecular chain end) is soluble in the free radical-polymerizable vinyl monomer capable of forming a hydrophilic polymer, or its mixture with the modifier monomer.

As the polymerization catalyst, there may be employed any of the known free radical initiators such as azobisisobutyronitrile, benzoyl peroxide, di-isopropylperoxy dicarbonate, ammonium persulfate and hydrogen peroxide. The copolymerization system may comprise at least one free radical-polymerizable vinyl monomer capable of forming a hydrophilic polymer, at least one hydrophobic macromolecular compound and, if desired, at least one modifier monomer. In order to fully utilize the characteristic properties of the hydrophilic compound, it is desirable that the total amount, in moles, of the modifier monomer be less than the amount, in moles, of the free radical-polymerizable vinyl monomer capable of forming a hydrophilic polymer. Further, in order to improve human body compatibility and other related properties, the purified material used to form the hydrogel, which is derived from the reaction product copolymer, should have an equilibrium water absorption of at least 10%, preferably at least 20%.

Except for the polymerization in bulk, the resulting copolymer can be processed by compression molding, extrusion molding or injection molding to obtain any desired article. A solution of the copolymer may be sometimes coated onto substrates composed of another material. In a special case, the copolymer is dissolved in a suitable hydrophilic monomer or a mixture thereof with a solvent, a polymerization initiator or cross-linking agent is added to the solution, and the resulting mixture is subjected to casting polymerization to obtain a shaped article.

The copolymer prepared using, as component (A), a vinyl ester should be saponified in a solvent capable of dissolving the copolymer such as methanol, methylethylketone or the like in the presence of a catalyst such as an alkali (for instance, sodium hydroxide) or an acid (for instance, sulfuric acid) at 0° to 100° C., preferably 10° to 60° C. according to a known method for the saponification of polyvinyl esters. If desired, it is possible to conduct the saponification at a temperature outside of the above range or in a heterogeneous system. In the case of a copolymer that can be especially easily saponified, for instance, a copolymer of vinyl formate or vinyl monochloroacetate, the saponification can be performed under milder conditions, and the vinyl ester units can be saponified selectively without decomposition of the ester linkages or ether linkages of the hydrophobic macromolecular compound units. A saponified copolymer obtained by saponifying the obtained copolymer to a saponification degree of at least 80 mole percent, preferably at least 95 mole percent, has especially high utility and has a high transparency comparable to that of PVA.

As is seen from the foregoing explanation, the material useful for forming a hydrogel, according to this invention, comprises a copolymer of a free radical-polymerizable vinyl monomer capable of forming a hydrophilic polymer with a hydrophobic macromolecular compound having a polymerizable double bond at its molecular chain end, and said copolymer, if desired, may further comprise a small amount of a third comonomer component and/or a cross-linking agent. This material forms a self-reinforcing hydrogel when it absorbs water and may be shaped into any appropriate form such as a film, sheet, tube, rod, fiber, granule or sponge.

The invention will be further illustrated by reference to the following examples, which are intended only to be illustrative, not limiting, in nature.

EXAMPLE 1

A 12% solution of n-butyl lithium in n-hexane was added dropwise to 500 ml of a benzene solution containing 0.04 ml of diphenylethylene until the reaction mixture exhibited a reddish brown color. Then, a solution of 4.8 ml ($6.2 \times 10^{-3}$ mole) of n-butyl lithium was added to the reaction mixture. 115 g (1.1 moles) of styrene was then added dropwise to the mixture while maintaining the mixture at $-50°$ C. by cooling or adjusting the styrene-dropping rate. After completion of the dropwise addition, the reaction mixture was maintained at this temperature for 30 minutes. Then, 0.88 g (0.02 mole) of ethylene oxide was added at $-20°$ C. and 2 ml (0.02 mole) of methacrylyl chloride was further added to effect the reaction. The resulting reaction mixture was added dropwise to methanol to precipitate the resulting polymer. A reactive styrene polymer (I) was obtained having a double bond at one end of its molecular chain. The molecular weight as measured by the vapor pressure osmotic method was 14,000, and the equilibrium water absorption ratio of this polymer was 1.0%. 4 g of this reactive styrene polymer (I) was dissolved in 120 ml of N,N-dimethylformamide (hereinafter abbreviated as "DMF"), and the resulting solution was charged into a glass ampoule under a nitrogen gas stream together with 30 g of 2-hydroxyethyl methacrylate, 0.09 g of ethyleneglycol dimethacrylate and 0.2 g of di-isopropylperoxy dicarbonate. The ampoule was sealed, and the polymerization was carried out for 30 hours in a thermostat bath maintained at 60° C. After completion of the polymerization reaction, the resulting polymer solution was added dropwise to benzene to obtain a copolymer. In the resulting copolymer, the content of the styrene polymer (I) was 6.7% by weight. The copolymer was dissolved in DMF and it was shaped into a transparent film by the casting method. The film was soaked in water for 7 days to attain the equilibrium state, and at this time the water absorption was 50.4% and the strength of the swollen film was 3.0 Kg/cm$^2$. In the case of a homopolymer free of styrene polymer (I), the equilibrium water absorption was 55.7% and the strength of the swollen film was 0.7 Kg/cm$^2$.

EXAMPLE 2

10 g of the same reactive styrene polymer (I) as used in Example 1 was dissolved in 70 ml of DMF, and this solution was charged into a glass ampoule under a nitrogen stream together with 15 g of 2-hydroxyethyl methacrylate, 0.05 g of ethyleneglycol dimethacrylate and 0.1 g of di-isopropylperoxy dicarbonate. The ampoule was sealed and the polymerization was carried out for 48 hours in a thermostat bath maintained at 60° C. The resulting polymer was purified in the same manner as in Example 1. The content of the styrene polymer (I) in the copolymer was 17.3% by weight. In the same manner as in Example 1, the copolymer was shaped into a film and the film was soaked in water to determine its properties in the form of a hydrogel. It was found that the equilibrium water absorption was 41.4% and the water-swollen film had a strength of 20.2 Kg/cm$^2$.

EXAMPLE 3

Each of the specimens of the copolymer obtained in Example 2, glass, polystyrene and poly(hydroxyethyl methacrylate) was placed in a watch glass, and was kept in a thermostat bath maintained at 37° C. 0.25 ml of fresh ACD blood of a dog was added dropwise to each specimen, and 0.025 ml of an aqueous solution containing calcium chloride in an amount of 0.1 mole per liter was added thereto to initiate the blood coagulation reaction. The blood mixture was well agitated and a glass sheet was employed to cover the watch glass. At appropriate intervals of time, distilled water was added to stop the reaction. The resulting blood clot wa soaked in water for 5 minutes, and it was dipped in a 37% aqueous solution of formaldehyde for 5 minutes. The clot was further washed with water to solidify it. The solidified clot was blotted between pieces of filter paper, and the weight was measured. The results are shown in FIG. 1. The amount of clot formed (%) on the ordinate was a relative value calculated based on the assumption that the maximum value of the weight of clot formed on the glass specimen was 100%.

From FIG. 1, it is seen that the anti-thrombogenic properties of the copolymer (curve 4) were excellent, and superior compared to those of the glass (curve 1), polystyrene (curve 2) and poly(hydroxyethyl methacrylate) (curve 3).

EXAMPLE 4

2000 ml of cyclohexane containing one drop of a diphenylethylene solution was partially reacted at 40° C. with a 12% solution of sec-butyl lithium in cyclohexane until a faint red color was observed in the mixture. At this point, 15 ml (0.02 mole) of sec-butyl lithium was added and then 281 g (2.7 moles) of styrene was added. The reaction mixture was maintained at 40° C. for 30 minutes and the living polystyrene was capped by treatment with a 7 ml of solution (0.035 mole) of di-phenylethylene, and then 3.0 g (0.04 mole) of allyl chloride was reacted with the terminal ends of the polystyrene. The resulting cyclohexane solution was poured into methanol to precipitate the resulting polymeric substance. The precipitated polymeric substance was separated by filtration, dried and pulverized to obtain a white powder. The number-average molecular weight of the white powder determined by the vapor pressure osmotic method was 13,000. The molecular weight distribution range was narrow and the value of $\overline{M}w/\overline{M}n$ (where $\overline{M}w$ and $\overline{M}n$ are weight-average and number-average molecular weights, respectively) was less than 1.06. The equilibrium water absorption was 0.9%. 3.3 g of this reactive polystyrene compound (II) was charged into a polymerization ampoule together with 12.1 g of vinyl acetate, 0.01 g of azobisisobutyronitrile and 7 ml of benzene. The inside atmosphere of the ampoule was replaced by nitrogen, and the polymerization was conducted at 60° C. for 24 hours. The yield of the resulting copolymer was 10.5 g.

1 g of the resulting copolymer was dissolved in 20 ml of methylethylketone, and to the solution was added 10 ml of a solution obtained by adding 40 g of sodium hydroxide to 1000 ml of methanol. Then, the mixture was allowed to stand at 50° C. for 4 hours. The precipitate was recovered by filtration, washed with methanol and subjected to Soxhlet extraction with methanol and benzene, respectively. The resulting saponified copolymer was insoluble in water and soluble in dimethyl sulfoxide (hereinafter referred to as "DMSO"). The chemical composition of the saponified copolymer was determined by employing the elementary analysis method and ultraviolet absorption spectroscopy and it was found that the content therein of the compound (II) was 8.8% by weight and the degree of saponification was 99.6 mole percent. The intrinsic viscosity ($\eta$) was 1.85 dl/g as measured in DMSO at 30° C.

EXAMPLE 5

A film was cast from a DMSO solution of the saponified copolymer obtained in Example 4, and this film was soaked in water maintained at 30° C. to determine its properties. The swollen film was transparent and tough, and it had a water absorption of 95.2%. For a comparative film of polyvinyl alcohol (PVA), the water absorption was 169.5%. Thus, it is apparent that the film of this Example had a highly improved water resistance.

Each of the test specimens of glass, PVA, the above saponified copolymer, polystyrene and medical grade silicone was soaked in water maintained at 30° C. and then a wet specimen of each was placed on a watch glass. The watch glass was kept in a thermostat bath maintained at 37° C. 0.25 ml of fresh ACD blood (acid-citrate dextrose solution) of a dog was added dropwise to each test specimen, and 0.025 ml of a 0.1 N aqueous solution of calcium chloride was added thereto to initiate the blood coagulation reaction. The blood mixture was well agitated and a glass plate was used to cover the watch glass. At certain time intervals, distilled water was added to stop the coagulation reaction. The resulting clot was soaked in water for 5 minutes and then placed in a 37% aqueous solution of formaldehyde for 5 minutes. Then, the clot was washed with water and thus solidified. The solidified clot was blotted between pieces of filter paper, and the weight was measured. The weight of the clot of each specimen was expressed in terms of a relative value calculated based on the assumption that the maximum weight of the clot formed on the glass specimen was 100%. The results are shown in Table 1.

TABLE 1

| Specimen | Amount of clot (% by weight) | |
| --- | --- | --- |
| | After 3 min. | After 6 min. |
| Saponified copolymer (this invention) | 2 | 50 |
| PVA (comparison) | 32 | 70 |

TABLE 1-continued

| Specimen | Amount of clot (% by weight) | |
|---|---|---|
| | After 3 min. | After 6 min. |
| Polystyrene (comparison) | 42 | 96 |

As is seen from Table 1, the rate of the blood coagulation reaction of the saponified copolymer of this invention was much lower than those of the comparative specimens (i.e., the saponified copolymer of this invention exhibited excellent anti-thrombogenic properties).

EXAMPLE 6

The permeability of water, uric acid and vitamin $B_{12}$ of the modified PVA film obtained in Example 4, PVA film and Cuprophane film (regenerated cellulose film sold by J. P. Bemberg Aktiengesellschaft, West Germany) was determined.

The results are shown in Table 2 below.

TABLE 2

| | Percent of water absorption (%) | Thickness* of film ($\mu$) | Permeability ($cm^2$/sec) | | |
|---|---|---|---|---|---|
| | | | Uric acid | Vitamin $B_{12}$ | Water |
| Modified PVA film obtained in Ex. 4 | 90 | 25 | $9.3 \times 10^{-7}$ | $15.9 \times 10^{-8}$ | $11.7 \times 10^{-6}$ |
| PVA film | — | 25 | $2.2 \times 10^{-7}$ | — | — |
| Cuprophane film | — | 25 | $5.6 \times 10^{-7}$ | $8.0 \times 10^{-8}$ | $7.4 \times 10^{-16}$ |

*At dry state

To amplify how the values in Table 2 were obtained, the measurement of the permeability of uric acid as an example was obtained as follows. Namely, an aqueous solution of uric acid and pure water were poured into two cells separated by the sample film, respectively, and the concentration of the uric acid was followed by means of U.V. spectroscopy.

From the observed concentration change, the permeability ($cm^2$/sec) was evaluated.

EXAMPLE 7

4 g of the same reactive styrene polymer (I) as used in Example 1 was dissolved in 120 ml of N,N-dimethylformamide, and the solution was charged into a glass ampoule under a nitrogen stream together with 16 g of N,N-dimethylacrylamide, 14 g of butyl acrylate and 0.2 g of di-isopropylperoxy dicarbonate. The ampoule was sealed and the polymerization was carried out for 30 hours in a thermostat bath maintained at 60° C. The resulting polymer solution was added dropwise to water, and the precipitate was washed with n-hexane to obtain a copolymer, in which the content of the reactive styrene polymer (I) was about 10% by weight. The copolymer was dissolved in dimethylformamide, and a transparent film was obtained from this solution by the casting method. When this film was soaked in water for 1 week to attain equilibrium, the water absorption was found to be 55%. The swollen film had a tensile strength of 35 Kg/$cm^2$. In the case of the comparative polymer free of the compound (I), the equilibrium water absorption was 70% and the tensile strength of the swollen film was only 3 Kg/$cm^2$.

EXAMPLE 8

5 g of the same reactive styrene polymer (I) as obtained in Example 1 was dissolved in 30 ml of dimethylformamide, and the resulting solution was charged into an ampoule under a nitrogen stream together with 8 g of diacetone acrylamide and 0.1 g of azobisisobutyronitrile. The ampoule was sealed and the polymerization was carried out for 30 hours in a thermostat bath maintained at 60° C. The polymer was purified in the same manner as in Example 1. The content of the compound (I) in the resulting copolymer was 20% by weight. In the same manner as in Example 1, a film was formed from this copolymer and dipped in water to determine the properties of the film as a hydrogel. The equilibrium water absorption was 35% and the tensile strength of the film swollen with water was 35.5 Kg/$cm^2$.

EXAMPLE 9

Each of the test pieces of the copolymer obtained in Example 8, glass, polystyrene, silicone rubber and polydiacetone-acrylamide was allowed to stand for more than 24 hours in water maintained at room temperature, and each was then placed in a watch glass and kept in a thermostat bath maintained at 37° C. 0.25 ml of fresh ACD blood of a dog was added dropwise to each of the test pieces, and 0.025 ml of an aqueous solution containing 0.1 mole per liter of calcium chloride was added to initiate the blood-coagulating reaction. The blood mixture was well agitated, and a glass sheet was used to cover each watch glass. At appropriate intervals of time, distilled water was added to stop the coagulation reaction. The resulting blood clot was soaked in water for 5 minutes and then placed in a 37% aqueous solution of formaldehyde for 5 minutes. The clot was washed with water and solidified. The solidified clot was blotted between pieces of filter paper and weighed. Assuming that the maximum value of the weight of the clot formed on the glass was 100 and that the clotting time at which the weight of the clot on each test piece was 50 was defined as t50, in the case of glass t50 was 2 minutes, in the case of polystyrene t50 was 2.5 minutes, in the case of poly-diacetoneacrylamide t50 was 3.5 minutes and in the case of silicone rubber t50 was 6 minutes. In the case of the copolymer obtained in Example 8, t50 was 6.5 minutes. From these results, it is seen that the material according to this invention has an excellent anti-thrombogenic property.

EXAMPLE 10

9.7 ml of a 35% hydrogen peroxide aqueous solution and 4.0 g of Mohr's salt ($FeSO_4 \cdot (NH_4)_2SO_4 \cdot 6H_2O$) were added to 50 ml of methylmethacrylate dissolved in 1000 ml of distilled water. After stirring for 10 hours under nitrogen, there was obtained poly-methylmethacrylate having a number average molecular weight of $2.2 \times 10^4$. It was confirmed that the thus-obtained polymer had one hydroxy group per molecule by Palits method (Palits et al., J. Macromol. Sci., C2, 225 (1968)). 5 g of said polymer was dissolved in 20 ml of pyridine and 1 ml of methacrylyl chloride was added to the solution. After stirring for 3 hours under nitrogen, the resultant solution was poured into methanol, and the product reactive polymer (III) was obtained as a precipitate. The yield of the product was 67%.

2.46 g of said reactive methyl methacrylate polymer (III) was dissolved in 14 ml of N,N-dimethylformamide, and the solution was charged into a glass ampoule under a nitrogen stream together with 1.23 g of hydroxyethyl methacrylate and 0.02 ml of a 50% hexane solution of di-isopropylperoxy dicarbonate. The ampoule was sealed and the polymerization was carried out for 22 hours at 60° C. The resulting solution was poured into a mixture of benzene/n-hexane (1/1 by weight), to yield a precipitate.

The precipitated product was confirmed to be a copolymer of hydroxyethyl methacrylate with poly-methyl-methacrylate, containing 56% by weight of methylmethacrylate units in the molecule by NMR spectroscopy and gel permeation chromatography.

The copolymer gave a clear, homogeneous film whose water absorption was 10% by casting a dimethylformamide solution thereof.

It was shown that the film had a micro-phase separation structure of hydrophilic and hydrophobic polymers. On the other hand, a film of a homopolymer mixture of hydroxyethylmethacrylate and methylmethacrylate was heterogeneous and opaque.

EXAMPLE 11

The reactive methyl methacrylate polymer (III) obtained in Example 10 and hydroxyethylmethacrylate (1:2 by weight ratio) were polymerized in dimethylformamide in the presence of di-isopropyl peroxydicarbonate to give a copolymer in 85% yield. The benzene soluble part was removed by extraction. The resulting copolymer contained 20% by weight of methyl methacrylate units, and gave a transparent film by casting from a dimethylformamide solution. The equilibrium absorption of the film was 40% and the tensile strength in the swollen state was 5.0 Kg/cm².

EXAMPLE 12

The anti-thrombogenic properties of the copolymer films obtained in Examples 10 and 11 and, for comparison, those of a random copolymer of hydroxyethyl methacrylate (HEMA) and methyl methacrylate (MMA), homopolymers of each monomer and a mixture of each homopolymer were evaluated by the same method as in Example 5. The results are shown in Table 3.

TABLE 3

| Specimen | Amount of clot-blood contact time 9 min. (% by weight) |
|---|---|
| Copolymer obtained in Example 10 | 35 |
| Copolymer obtained in Example 11 | 37 |
| Random copolymer of HEMA and MMA (MMA 44% by weight) | 88 |
| Homopolymer of HEMA | 60 |
| Homopolymer of MMA | 82 |
| Homopolymer mixture of HEMA and MMA (1:1 by weight) | 72 |
| Medical grade silicone | 50 |

EXAMPLE 13

5.0 g of each of the copolymers obtained in Examples 1 and 2 were dissolved respectively in a mixed solvent of 7.0 ml of tetrahydrofuran and 3.0 ml of methanol, and 50 g of 2-hydroxyethyl methacrylate, 0.25 g of ethyleneglycol dimethacrylate and 0.2 g of t-butyl peroctoate were added to each solution. The polymerization was carried out for 24 hours in a thermostat bath maintained at 60° C. When the resulting copolymer was allowed to adsorb water, a colorless, transparent, self-reinforcing hydrogel was formed.

EXAMPLE 14

4.0 g of each of the copolymers obtained in Examples 1 and 11 were respectively placed in a mould frame having a diameter of 2 cm and a depth of 0.6 cm. The copolymers were molten at 167° C. under 35 atmospheres of pressure and a colorless, transparent, lens-like disc was obtained. A self-reinforcing hydrogel was obtained by swelling this disc in water.

What is claimed:

1. A copolymer for a self-reinforced and highly biocompatible hydrogel which comprises (1) a hydrophilic polymer backbone moiety from a free radical polymerizable vinyl monomer capable of forming a hydrophilic polymer and (2) graft moieties attached to said backbone moiety from a hydrophobic macromolecular compound, 5 to 80% based on the weight of the copolymer, having a chain-terminated polymerizable double bond and a molecular weight of 1,000 to 100,000, said copolymer being swelled with water in a degree of an equilibrium water absorption of at least 10% by weight.

2. A copolymer as defined by claim 1, wherein said free radical-polymerizable monomer capable of forming a hydrophilic polymer is a monomer represented by the general formula:

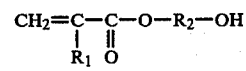

wherein $R_1$ represents a hydrogen atom or a methyl group, wherein $R_2$ is an alkylene group or $-CH_2CH_2(OCH_2CH_2)_n-$, and wherein n is an integer of 1 to 30.

3. A copolymer as defined by claim 1, wherein said hydrophobic macromolecular compound is polystyrene.

4. A copolymer as defined by claim 1, wherein said hydrophobic macromolecular compound is selected from the group consisting of polymethyl methacrylate and polymethyl acrylate.

5. Articles for biomedical purposes prepared from the copolymer of claim 1.

6. A hydrogel material having a degree of water absorption of at least 10% by weight consisting essentially of a copolymer comprising (1) a backbone moiety of a monomer of the formula:

$$CH_2=C-C-O-R_2-OH$$
$$\phantom{CH_2=C}|\phantom{C}\|$$
$$\phantom{CH_2=}R_1\phantom{C-}O$$

wherein $R_1$ is a hydrogen atom or a methyl group, wherein $R_2$ is an alkylene group or $-CH_2CH_2(OCH_2CH_2)_n-$, and wherein n is an integer of 1 to 30 and (2) graft moieties attached to said backbone moiety of a hydrophobic polymer having a chain terminated polymerizable double bond and a molecular weight of from 1,000 to 100,000.

7. A hydrogel material as defined by claim 6, wherein said hydrophobic polymer is selected from the group consisting of polystyrene and poly-α-methylstyrene.

8. A hydrogel material as defined by claim 6, wherein said hydrophobic polymer is selected from the group consisting of polymethyl methacrylate and polymethyl acrylate.

9. A hydrogel material as defined in claim 6, wherein said hydrophobic polymer is represented by the formula:

$$R+CH_2-CH)_n CH_2-CX=CH_2$$
$$\phantom{R+CH_2-CH)}|$$
$$\phantom{R+CH_2-CH)}C_6H_5$$

or $$R+CH_2-CH)_n CH_2-CH_2-O-C-CX=CH_2$$
$$\phantom{R+CH_2-CH)}|\phantom{CH_2-CH_2-O-}\|$$
$$\phantom{R+CH_2-CH)}C_6H_5\phantom{CH_2-CH_2-O}O$$

wherein R is an alkyl group, X is a hydrogen atom or an alkyl group and wherein n is an integer of from 10 to 1,000.

10. A hydrogel material as defined by claim 6, wherein said monomer is selected from the group consisting of hydroxyethyl acrylate, hydroxyethyl methacrylate, hydroxypropyl acrylate, hydroxypropyl methacrylate, hydroxybutyl acrylate, hydroxybutyl methacrylate, polyethylene glycol monoacrylate and polyethylene glycol monomethacrylate.

11. A shaped article prepared from the hydrogel material as defined by claim 6.

12. A hydrogel material as defined by claim 10, wherein said copolymer also contains an amount of a comonomer which is copolymerizable with said monomer, said amount, in moles, being less than the amount, in moles, of said monomer wherein said copolymerizable monomer is selected from the group consisting of acrylic acid, methacrylic acid, methoxyethyl acrylate, methoxyethyl methacrylate, ethyl acrylate, ethyl methacrylate, propyl acrylate, propyl methacrylate, n-butyl acrylate, n-butyl methacrylate, α-methylstyrene, ethylene, propylene, butene, isoprene, butadiene, and maleic anhydride.

13. A hydrogel material as defined by claim 6, wherein said first monomer is 2-hydroxyethyl methacrylate and said hydrophobic polymer is represented by the formula:

$$R+CH_2-CH)_n CH_2-CH_2-O-C-CX=CH_2$$
$$\phantom{R+CH_2-CH)}|\phantom{CH_2-CH_2-O-}\|$$
$$\phantom{R+CH_2-CH)}C_6H_5\phantom{CH_2-CH_2-O}O$$

wherein R is an alkyl group, X is a hydrogen atom or an alkyl group, and wherein n is an integer which represents a molecular weight of 1,000 to 100,000.

* * * * *